United States Patent

Craig

[11] 4,000,425
[45] Dec. 28, 1976

[54] APPARATUS FOR PRODUCING AXIAL TOMOGRAMS

[76] Inventor: Dwin R. Craig, 9447 Emory Grove Road, Gaithersburg, Md. 20760

[22] Filed: Aug. 1, 1975

[21] Appl. No.: 601,088

[52] U.S. Cl. .......................... 250/445 T; 250/446
[51] Int. Cl.² ........................................ G01N 21/34
[58] Field of Search ............ 250/445 T, 358 P, 446

[56] References Cited

UNITED STATES PATENTS

| 2,396,069 | 3/1946 | Zapp | 250/358 P |
| 2,789,231 | 4/1957 | Dumer | 250/446 |
| 3,867,634 | 2/1975 | Hounsfield | 250/445 T |
| 3,928,769 | 12/1975 | Smith | 250/445 T |

Primary Examiner—Davis L. Willis
Attorney, Agent, or Firm—Blair & Brown

[57] ABSTRACT

The present invention relates to the formation of a tomogram by means of apparatus which will expose a photosensitive surface edgewise by means of an X-ray source which passes through a subject with the subject and the film being rotated about parallel vertical axes transverse to the X-ray beam.

10 Claims, 6 Drawing Figures

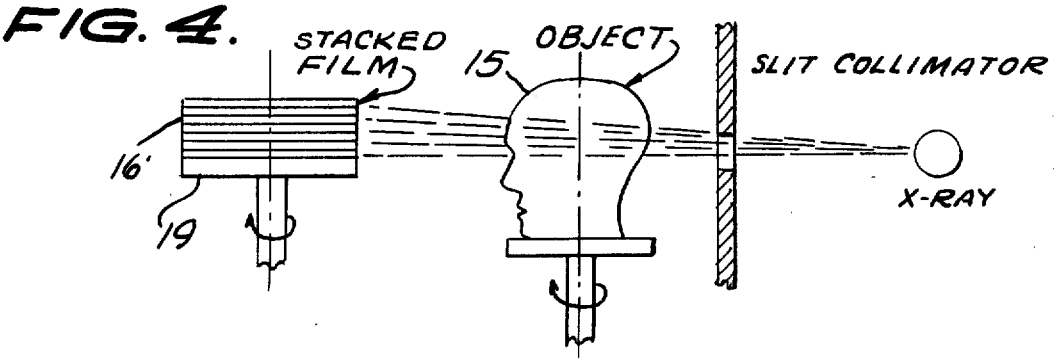
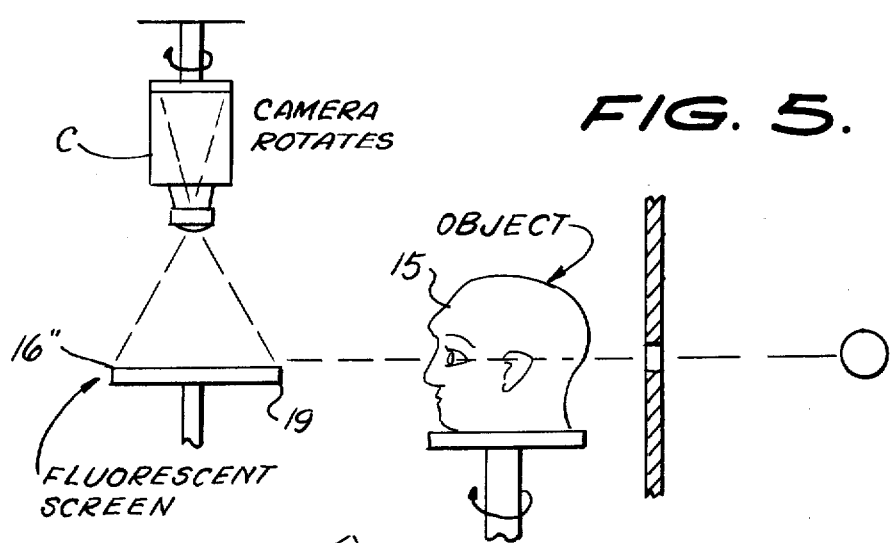
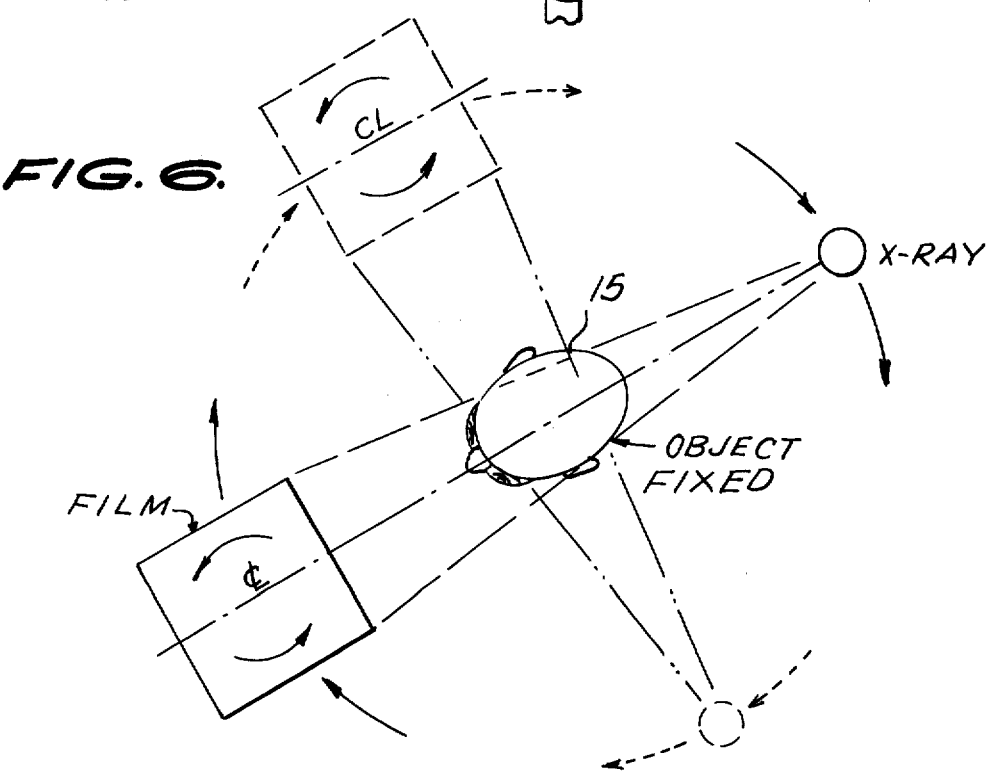

APPARATUS FOR PRODUCING AXIAL TOMOGRAMS

BACKGROUND OF THE INVENTION

1. Field of the Invention

The present invention relates to apparatus for producing axial tomograms which consists of an X-ray sectional view of an object.

2. Summary of the Invention

This invention relates to apparatus which can produce a cross-sectional view of an object on any photosensitive surface responsive to electro-magnetic radiation having wavelengths able to penetrate the object. The cross-sectional view is obtained after a time exposure of the photosensitive surface during which synchronized rotary motion about parallel axes is imparted to at least two of the three elements identified as follows:

a. the radiation source
   b. the object whose cross-sectional view is desired
   c. the photosensitive surface.

Of particular interest is the case where the radiation source is an X-ray tube, the object is the skull of a living human being and the photosensitive surface is a sheet of X-ray film. Proper rotary motion of the skull and film during exposure will produce a film image, after development, representing a cross section of the skull as if it had been sliced by a plane above and parallel to the ears, permitting the upper portion to be removed and the contents to be viewed from above. For clarity here, a second analogy would be similar to sawing through the trunk of a tree so that the growth rings can be observed. Here, of course, the cross-section view is obtained by imaging X-rays without the need for physical sawing or slicing.

In current X-ray technology, the closest approach to the present invention is apparatus for generating what is alternately termed a "laminogram" or a tomogram. Such apparatus places the X-ray tube and the film on opposite sides of the object with the surface of the film facing the X-ray tube. During a time exposure, the X-ray tube and the film are simultaneously translated in parallel planes in opposite directions and at different rates.

The rates and distances are chosen so that only those features within the object which lie in one plane are imaged sharply on the film. All features above or below this plane are "blurred" during the exposure.

In short, the film which is able to integrate with respect to time and to space has performed the computer function known as "autocorrelation" in the process of producing the tomogram. The traditional tomogram, produced by the apparatus just described, produces that view which we see as the grain in a length of lumber after a tree emerges from the sawmill. By contrast, the present invention produces a view which is observed by inspecting the end of the same piece of lumber. Consistent with prior nomenclature, the end view or cross-section view obtained by X-rays will be called an "axial tomogram." Prior art devices are available which produce "computerized axial tomograms," using X-rays on human beings. The known prior art systems operate on the same basic principle in producing an axial tomogram of the brain and can be briefly described as follows.

A pencil beam of X-rays is formed by an X-ray source and a photoelectric detector situated on opposite sides of the skull which is held stationary during a five minute time exposure. During exposure the source and detector scan in synchronism along parallel paths in a straight line translating motion. After each such pass the source and detector are repositioned so that the pencil beam is rotated approximately through an angle of one degree relative to the backbone of the patient, after which the linear motion of the source and detector are reversed to make another pass. This procedure is repeated so that the combination of rotation and translation makes about 180 passes to produce a total rotation of 180°. The total scanning time requires about five minutes due to the large masses being moved in a reciprocating and angularly stepped motion. During exposure, the photoelectric detector continually sends signals to a digital computer which samples the electrical signal about 180 times during each pass and converts the signal to a digital number which is stored on a magnetic disc. Upon recall, the computer generates a picture on a cathode ray tube composed of a checkerboard matrix of picture elements on the order of 180 × 180 for a total of 32,000 elements. The resolution of commercial television which produces a 525 × 525 image for a total of 275,000 picutre elements is 8.6 times as good. By the same criteria, X-ray film can produce an image composed of at least ten million picture elements which is about 300 times that produced by (C.A.T.) computerized axial tomography. Moreover, both devices described above are extremely expensive.

One objective of the present invention is to produce an axial tomogram on film having the following comparative specifications:

| Apparatus | C. A. T. | Invention |
|---|---|---|
| Scan Time | 5 minutes | 10 seconds |
| Picture Elements | 32,000 | 10,000,000 |
| Price | 10 × | × |
| Patient Position | Prone | Seated |
| Total Scan Angle | 180° | 360° |
| Scan Pattern | Reciprocating plus Rotary | Pure Rotary |
| Information Flow | Digital | Continuous |

Although the subsequent description of the present invention is confined, for the sake of clarity, to apparatus for producing axial tomograms of the human brain by means of X-rays, it should be emphasized that other parts of the body can be imaged by similar apparatus. It should be further emphasized that inanimate objects can be likewise imaged by X-rays or any other form of radiation which can penetrate the object and also produce a physical change on a detecting surface.

The radiating wavelengths include microwave frequencies, infra-red, visible light, ultraviolet, high energy electrons, X-rays and gamma rays all of which can be made to emanate from a point source. The choice of wavelengths will depend on the material of which the object is made. The detector surface may include film which is exposed directly by the radiation, a fluorescent surface which indirectly exposes film by either contact or projection, an image converter which responds to the radiation and through electron emission produces an image on a fluorescent screen, a surface which is electrically charged and then locally discharged by the radiation to form a charge pattern.

The primary object of the invention is to provide a low cost high speed apparatus for producing tomograms.

BRIEF DESCRIPTION OF THE DRAWINGS

FIG. 4 is another slight modification of the invention illustrated in FIG. 1 showing the use of stacked film;

FIG. 5 is a further modification of the invention illustrated in FIG. 1 with the X-ray source energizing a fluorescent screen photographed by a rotating camera; and FIG. 6 is a still further modification of the invention in which the subject is fixed and the X-ray source as well as the film rotates around the subject.

DESCRIPTION OF THE PREFERRED EMBODIMENTS

Figure 1:
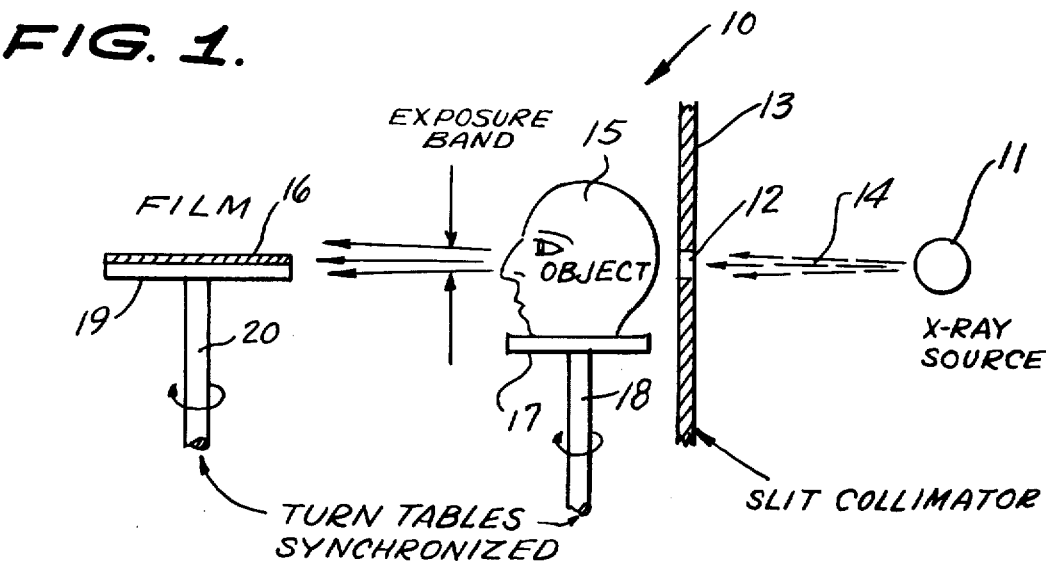
FIG. 1 is a side elevation of the invention.

Referring now to the drawings in detail wherein like reference characters indicate like parts throughout the several figures, the reference numeral 10 indicates generally an apparatus constructed in accordance with the invention. The apparatus 10 includes a point source of X-ray beams 11 which pass through a slit opening 12 in a plate 13 impervious to the rays 14 emanating from the X-ray source 11. A subject 15 is penetrated by the rays 14 and exposes a film 16 which is mounted in a plane corresponding to the plane of the slit 12. For clarity the subject 15 (a human skull) is shown detached from its body and mounted on a turntable 17 having a vertical axis 18. The X-ray film 16 is also mounted on a turntable 19 having an axis 20 above which it rotates. The turntables 17–19 have their axes 18–20 parallel with the film 16 lying in the same plane as the fan-shaped beam 14. The turntables 17–19 are rotated in synchronism by conventional means (not shown). In conventional X-ray exposure the rays 14 arrive normal to the surface of the film, whereas in the instant invention the rays arrive substantially parallel to the plane of the film.

Figure 2:
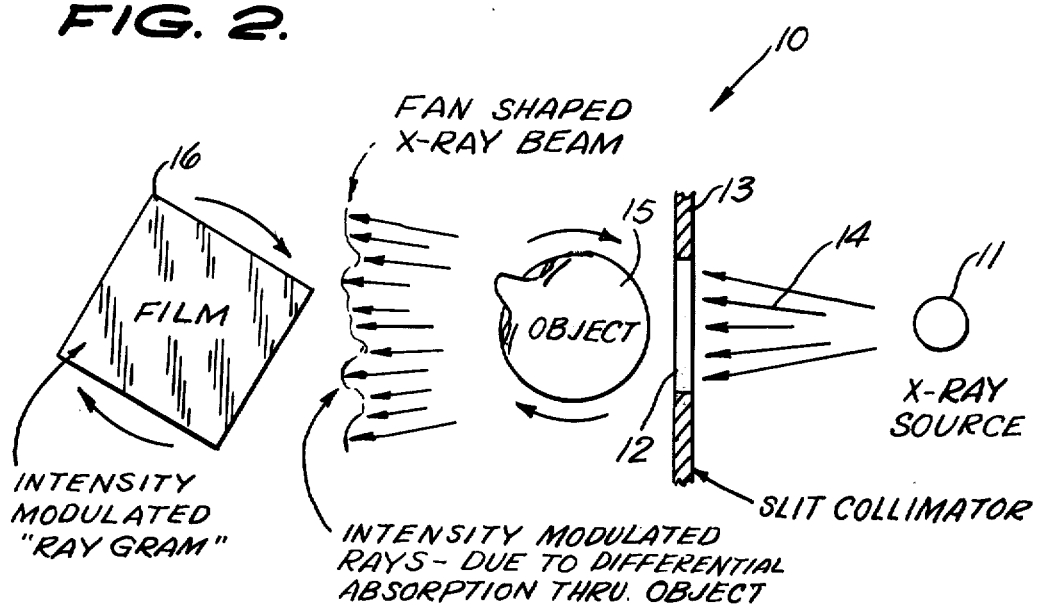
FIG. 2 is a top plan view of the invention.

An instantaneous exposure would produce what might be termed as "raygram" composed of long shadows cast on the film by differential penetration of rays passing through various portions of the skull as shown in the plan view of FIG. 2.

During a time exposure, the two turntables are coupled to rotate in synchronism through a full 360° revolution while the film is continuously recording "raygrams." The resulting composite exposure of "raygrams" produces the desired axial tomogram, reproducing the cross-section view with great geometric fidelity and high resolution — limited only by the precision of the mechanical motions involved. Since only rotary motion is employed, freedom from vibration and backlash inherently permits smooth and precise synchronous motion of the two turntables.

Figure 3:
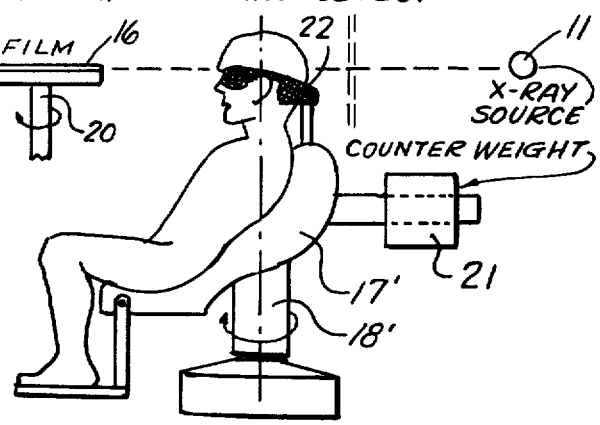
FIG. 3 is a slight modification of the invention illustrated in FIGS. 1 and 2 in which the object is seated in a chair.

As shown in FIG. 3, the skull turntable is actually a reclining chair 17' having a turning axis 18' and a counterweight 21. Suitable clamps 22 hold the comfortably seated patient with his skull rigid with respect to the chair. The preferred contact points for clamping are at the base of the skull and at the cheekbones, leaving the jaw free for yawning, and swallowing, etc.

The chair 17' instead of rotating about the center of gravity of its contents, is counter weighted so that rotation is about an axis 18' which passes upwardly through the approximate center of the skull. Any horizontal displacement of the axis of rotation and the center of the skull simply produces a corresponding displacement of the tomogram on the film.

Since diagnostic X-rays are essentially exploratory, the search for an anomoly requires a number of "slices" before locating the cross-section of interest. In FIG. 4 a slight modification of the invention is illustrated wherein a stack 16' of film is positioned on the turntable 19 with all of the stack being exposed simultaneously during a single revolution of the film and subject. The number of films and the separation between the sheets will determine the recorded number and spacing of "slices" through the skull. Obviously the number can be large and the spacing can be small. Since the sheets of film are held in registry during exposure, they all reproduce identical geometry and scale and can be subsequently viewed in register for greatly enhanced contrast.

For greater sensitivity, the film separators would be fluorescent screens as conventionally used in medical X-ray laboratories for indirect exposure of the film.

A further modified form of the invention is illustrated in FIG. 5 wherein the fan-shaped beam is directed toward the edge of a fluorescent surface 16" which is supported on the turntable 19 and can be rotated or fixed since the fluorescent image is transitory. The screen is observed by a camera C which rotates in synchronism with the skull. The camera C may use an image intensifier or not, it may contain in its focal plane conventional photographic film, Polaroid film, a charge storage surface or a television camera tube.

Until now, the X-ray source has been held stationary while the skull and film rotate. It should be obvious that the axes of rotation need not be vertical, but need only be parallel. Also, the rotational rates need not be constant as long as the two turntables are always synchronized. Rotational rates can be programmed to normalize exposure when scanning objects of oblong cross-section. Only proper relative motion is important.

A still further modified form of the invention is illustrated in FIG. 6 wherein the skull 15 is fixed while the X-ray source and the film orbit about the center of the skull. In addition the film must rotate with respect to its own supporting structure so that a centerline passing through the skull initially defines a centerline on the film, with the two centerlines being maintained parallel throughout the entire revolution.

Although the mechanical consequences of orbiting source and detector become extremely cumbersome, its application becomes necessary when the object cannot be conveniently rotated e.g. installed pipe lines, structural supports and other mechanically fixed or immobile objects.

The radiation source may be a continuous emitter or may be pulsed. If pulsed, the repetition rate will govern the time allowed for one revolution to produce the desired number of "raygrams" comprising the tomogram. For example, a pulse rate of 60 cycles per second and a scan time of 10 seconds for one revolution will produce a tomogram comprised of 600 raygrams. On the other hand, a continuous source would produce a tomogram comprised of an infinite number of raygrams in which resolution of the image would be limited only by resolution of the detecting surface.

Having thus described the preferred embodiments of the invention it should be understood that numerous structural modifications and adaptations may be resorted to without departing from the spirit of the invention.

What is claimed is:

1. An apparatus for producing axial tomograms including:
   a point source of electromagnetic radiation:
   means for confining a portion of said radiation to a thin, fan-shaped beam:
   means for supporting an object in the beam, wherein said object allows differential penetration of said radiation:
   means for supporting and rotating a flat radiation detecting surface in and substantially parallel to the plane of said beam after penetration of said object wherein said surface is capable of forming a raygram image of said differential penetration:
   means for relative rotational drive of said object support, said point source and said surface support, about parallel axes which pass at right angles through the plane of said fan-shaped beam: and
   means for synchronizing said relative rotation.

2. A device as claimed in claim 1 wherein said radiation source emits X-rays.

3. A device as claimed in claim 1 wherein the object is a portion of the human body.

4. A device as claimed in claim 1 wherein the surface is photographic film.

5. A device as claimed in claim 1 wherein said surface comprises a plurality of stacked surfaces.

6. A device as claimed in claim 1 wherein said surface is a fluorescent screen and a camera is focused to view said fluorescent screen.

7. A device as claimed in claim 1 wherein the object is a human skull and the object support is a rotatable reclining chair.

8. A device as claimed in claim 1 wherein said rotational rates are programmed to normalize exposure.

9. A device as claimed in claim 1 wherein said radiation source is stationary and said object support and said surface support are rotated in synchronism in the same direction along parallel axes.

10. A device as claimed in claim 1 wherein said object is fixed with said radiation source and said surface support positioned on opposite sides of said object and rotating about said object said surface support rotating so that its horizontal centerline remains parallel to the centerline therethrough at the beginning point.

* * * * *